US008883492B2

(12) United States Patent
Kobayashi et al.

(10) Patent No.: US 8,883,492 B2
(45) Date of Patent: Nov. 11, 2014

(54) CELL CULTURE APPARATUS

(75) Inventors: Toyoshige Kobayashi, Fujimino (JP);
Ryota Nakajima, Tsurugashima (JP);
Takayuki Nozaki, Kawagoe (JP); Shizu Matsuoka, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 290 days.

(21) Appl. No.: 13/331,237

(22) Filed: Dec. 20, 2011

(65) Prior Publication Data

US 2012/0164721 A1 Jun. 28, 2012

(30) Foreign Application Priority Data

Dec. 22, 2010 (JP) ................. 2010-285849

(51) Int. Cl.
*C12M 1/00* (2006.01)
*C12M 1/34* (2006.01)
*C12M 3/00* (2006.01)

(52) U.S. Cl.
CPC ..................... *C12M 41/14* (2013.01)
USPC .................. 435/289.1; 435/283.1; 435/288.5; 435/288.4; 435/288.3

(58) Field of Classification Search
USPC ........................... 435/283.1–309.4
See application file for complete search history.

(56) References Cited

U.S. PATENT DOCUMENTS

| 6,228,635 | B1* | 5/2001 | Armstrong et al. ........ 435/286.5 |
| 2004/0077072 | A1 | 4/2004 | Takagi et al. |
| 2006/0023299 | A1 | 2/2006 | Muraki |
| 2006/0115889 | A1 | 6/2006 | Nakashima et al. |
| 2006/0194193 | A1* | 8/2006 | Tsuruta et al. .................... 435/4 |
| 2009/0298129 | A1* | 12/2009 | Spence et al. ................ 435/91.2 |
| 2010/0105138 | A1 | 4/2010 | Dodd et al. |
| 2010/0291663 | A1 | 11/2010 | Koshiba |

FOREIGN PATENT DOCUMENTS

| JP | 2002-315566 A | 10/2002 |
| JP | 2006-149268 A | 6/2006 |

* cited by examiner

*Primary Examiner* — Nathan Bowers
*Assistant Examiner* — Lydia Edwards
(74) *Attorney, Agent, or Firm* — Mattingly & Malur, PC

(57) ABSTRACT

A cell culture apparatus has four sections, including a cell culture chamber, refrigerator, control unit, and intermediate chamber. The cell culture chamber includes a culture vessel base as a holding member for holding and installing a culture vessel, a microscope for photographing a cell image within the culture vessel, and a drive base which has drive mechanisms such as a pump and a valve to be connected to a flow channel having a closed structure including a tank. With the drive base within the cell culture chamber as the center, the rotatable culture vessel is arranged in the horizontal direction and the refrigerator in which the culture medium base containing the cell fluid and culture medium is installed is arranged in the vertical direction. The arrangement configuration is space-saving and provides a short distance between the instruments.

13 Claims, 12 Drawing Sheets

CELL CULTURE APPARATUS

CLAIM OF PRIORITY

The present application claims priority from Japanese patent application JP2010-285849 filed on Dec. 22, 2010, the content of which is hereby incorporated by reference into this application.

BACKGROUND OF THE INVENTION

The present invention relates to a cell culture apparatus for culturing cells and in particular to an automatic culturing technology for culturing cells efficiently with aseptic cleanliness.

Cell culture operations have been performed by hand by skilled operators under severe manufacturing processes within utterly disinfected clean rooms. When cells are cultured in large quantities aiming at industrialization, therefore, there are possibilities of the occurrence of increases in burdens on operators, time and cost required for training operators, human errors and sample mix-ups, and biological pollution (contamination) by humans carrying bacteria, requiring considerable cost for taking countermeasures. That is an obstacle to the industrialization of mass cell culture.

It is therefore expected that these problems will be solved by automating a series of culture operations by instruments. Currently automatic culture apparatuses following manual culture operations using articulated robot manipulators are mainly developed. Manual culture operations are, however, performed by complicated actions. In such culture apparatuses it is required to perform handling of culture vessels and culture fluids aseptically equally with manual operations or in a simplified manner.

To this end, for example, Japanese Patent Application Laid-Open Publication No. 2006-149268 provides an example for performing transfer operations for a culture vessel and culture medium exchange by an articulated robot manipulator. It is shown that the articulated robot manipulator itself can be sterilized.

As another example, Japanese Patent Application Laid-Open Publication No. 2002-315566 provides a processing method with a culture vessel and a flow channel system themselves hermetically sealed. The method hermetically seals the culture vessel and the flow channel and takes out the culture vessel and partly capped flow channel in such a manner they are not exposed to the outside air after the end of culture in an apparatus for culturing cartilage cells by applying high pressure thereto, in which means for collecting aseptically produced cartilaginous tissue is provided.

BRIEF SUMMARY OF THE INVENTION

In an automatic culture apparatus like one described in Japanese Patent Application Laid-Open Publication No. 2006-149268, an operation to open the inside of the culture vessel by opening a lid is necessary because the culture vessel itself is an open system. Thus, the upsizing of air-conditioning equipment is involved in order to maintain the cleanliness of the inside of the automatic culture apparatus, thereby causing the upsizing of the entire system and increasing cost.

In an automatic culture apparatus like one described in Japanese Patent Application Laid-Open Publication No. 2002-315566, because of its hermetically sealed system, there are problems of how to install a flow channel with the internal asepsis maintained and inject a culture medium (a culture fluid) and cells (a cell suspension) into the flow channel. There is another problem of how to, in performing complicated culturing operations, install the hermetically sealed flow channel in the apparatus and give driving force efficiently.

Currently in generative medicine using human cells and transplanting cells and tissue prepared by culture into humans, tissue extracted in an operating room is put into an aseptically treated test tube or the like and is carried out with its inside maintained to be aseptic, then necessary cells are isolated from the tissue in the Cell Processing Center (CPC) conforming to the Good Manufacturing Practice (GMP) and are cultured under desired adjustments. In order to culture the extracted cells with no pollution in the manufacturing process, they have to be manufactured manually under a process and an environment satisfying very strict regulations. Even in an automatic culture apparatus which performs cell culturing automatically by machine, cells or tissue manufactured by the apparatus have to be free from any biological pollution caused by bacteria and viruses in the manufacturing process. Under such a condition, when considering the system of the above-described automatic culture apparatus using the open-system culture vessel, in order to sterilize the inside of the automatic culture apparatus to maintain a highly clean environment of the inside, huge air-conditioning equipment and sterilizing equipment are required, and hence cost for the equipment itself is required. A drive system such as motor cannot endure during sterilization.

A system is preferred in which a culture vessel for automatic culturing itself is made to be a closed-system structure, its inside can be sterilized, and cells are cultured by externally supplying driving force. In order to perform culturing with a culture vessel having a closed-system structure, however, there is a problem of how to improve the efficiency of a mechanism and a control method for aseptically putting a cell culture and cells thereinto and performing culturing.

The present invention provides, in order to solve the above-described problems, a cell culture apparatus which can prepare tissue using cells and aims at conformity to the GMP and further a cell culture apparatus provided with the configuration of components and a closed-system flow channel, space-saving arrangements, and an aseptic fluid conveying mechanism for the flow channel.

According to one aspect of the present invention, there is provided a cell culture apparatus for culturing cells using a culture medium, including: a plurality of flow channels for delivering the culture medium and the cells; a drive base arranged within a first space; a culture vessel connected to the drive base through the flow channels; a holding member for holding the culture vessel; a refrigerating unit which is formed below the drive base to form a refrigerating space; and an intermediate chamber for separating the first space and the refrigerating space.

According to another aspect of the present invention, there is provided a cell culture apparatus for culturing cells, including: a plurality of flow channels for delivering a culture medium and a cell fluid; a drive base arranged within a first space; a culture vessel connected to the drive base through the flow channels; a culture vessel base which is arranged in a second quadrant with respect to the first space and in which the culture vessel is installed; a refrigerating unit for refrigerating the culture medium and the cell fluid; and an intermediate chamber which is positioned below the drive base and in a fourth quadrant with respect to the first space and separates the refrigerating unit installed therein and the first space.

The present invention can achieve a cell culture apparatus which is provided with the installability of a closed-system flow channel having a culture vessel to culture cells efficiently aseptically with aseptic cleanliness with a GMP level.

DETAILED DESCRIPTION OF THE INVENTION

Figure 1:
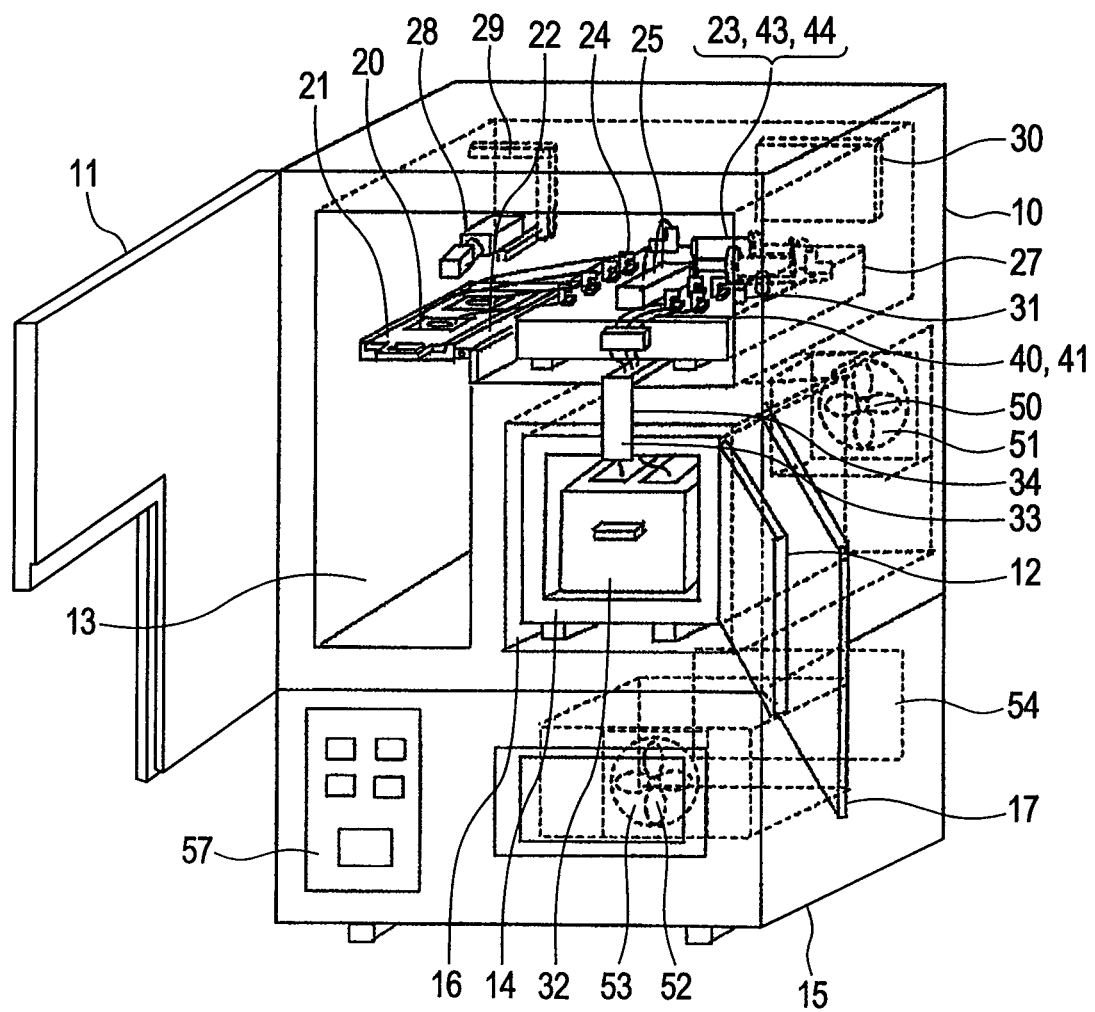
FIG. 1 shows the overall brief configuration of an automatic culture apparatus in which a drive base is installed in accordance with the first embodiment of the present invention.

Hereinafter, an embodiment of the present invention will be described with reference to the attached drawings. Prior to the detailed description of the embodiment of the present invention, the summary of the present invention will be provided as follows.

In the best mode of the automatic culture apparatus, using a closed-system flow channel and a mechanism called a drive base for fluid delivery within the closed-system flow channel, a cell fluid and a culture medium within a refrigerator (at around 4° C.) within the apparatus are heated within a culture chamber (at around 37° C.) to be delivered to a cell culture space within a culture vessel. To this end, the closed-system flow channel includes mainly three modules: a culture medium module by the cell fluid and culture medium, which are required to be refrigerated at 5° C., a cleaning fluid, and a waste fluid; a drive module for delivering those fluids to the culture chamber by a pump and heating them up to 37° C. in a tank; and a culture vessel module for delivering the cell fluid and culture medium from the tank to the culture space within the culture vessel to perform culturing. A microscope is arranged in the vicinity of the culture chamber module to photograph the cells on a culture surface. Each module is installed in a holder having a drive mechanism in its part, each of which is called base. The base, which is integral with the closed-system flow channel, is taken out of and put into the inside of the culture apparatus by a removable carrier. The inside of the automatic culture apparatus includes the culture vessel, a refrigerating chamber, and their intermediate chamber, each of which has a door. The refrigerating chamber is kept at around 4° C., and the inside of the culture chamber is kept at a temperature of 37° C., a carbon dioxide concentration of 5%, and a humidity of nearly 100%. The refrigerating chamber includes containers for a cell suspension, a culture medium, a cleaning fluid, and a waste fluid and a waste fluid collection port equipped with a check valve. In order to prevent the occurrence of water condensation and temperature variations caused by the direct connection between the inside of the culture chamber and the inside of the refrigerating chamber which have entirely different environments, the intermediate chamber is provided between them, thereby separating them by a seal such as a rubber stopper except for a fluid delivering tube. The intermediate chamber is provided with a fan having a filter, allowing the environment outside the automatic culture apparatus to be maintained. Entirely different but ideal environments for cells are thereby installed in the same apparatus, achieving space saving.

By moving the base close to a safety cabinet (or a clean bench) by the carrier, sterilizing an empty bag within the closed-system flow channel the inside of which is sterilized and putting it into the inside of the safety cabinet, injecting the cell suspension (or the culture medium and the cleaning fluid) into the inside of bags, and sealing an injection port, the inside of the closed-system flow channel is maintained at an aseptic condition regardless of the environment outside the closed-system flow channel. In the method of the present invention, when the closed-system flow channel is put into the automatic culture apparatus together with the base, automatic cell culture operations including cell seeding, culture medium exchange, microscopic observation, and waste fluid collection for inspection can be performed while maintaining the inside of the closed-system flow channel regardless of the installation place of the automatic culture apparatus, because a drive mechanism is installed outside the closed-system flow channel.

Another aspect of the present invention will be revealed by the following embodiment which will be described in detail with reference to the attached drawings. It is noted that the present embodiment is a merely one example for achieving the present invention and that it does not limit the technical scope of the present invention. Throughout the drawings, like reference numerals refer to like components.

First Embodiment

Figure 2:
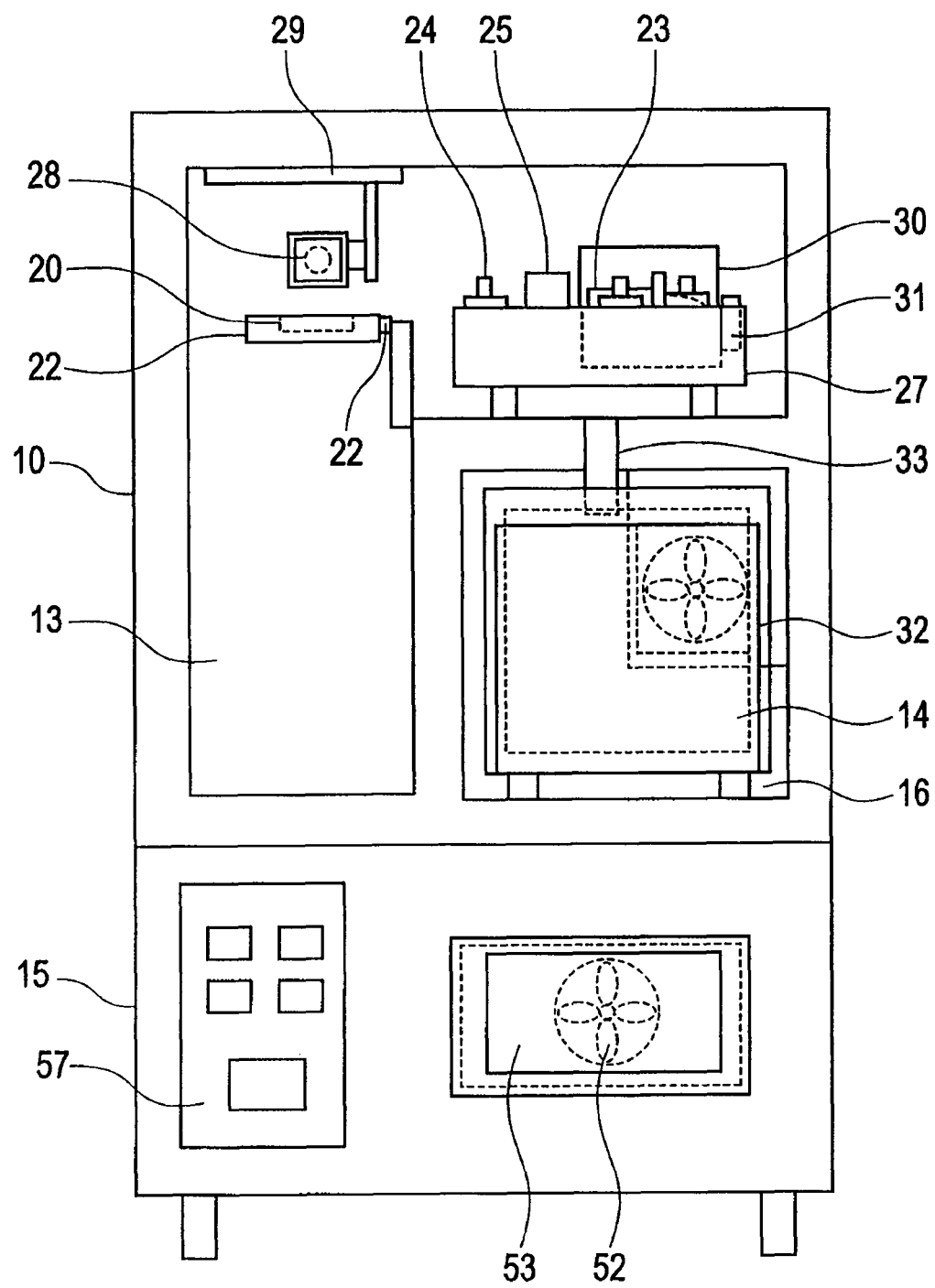
FIG. 2 is a front view showing the automatic culture apparatus with a door open in accordance with the first embodiment.
Figure 3:
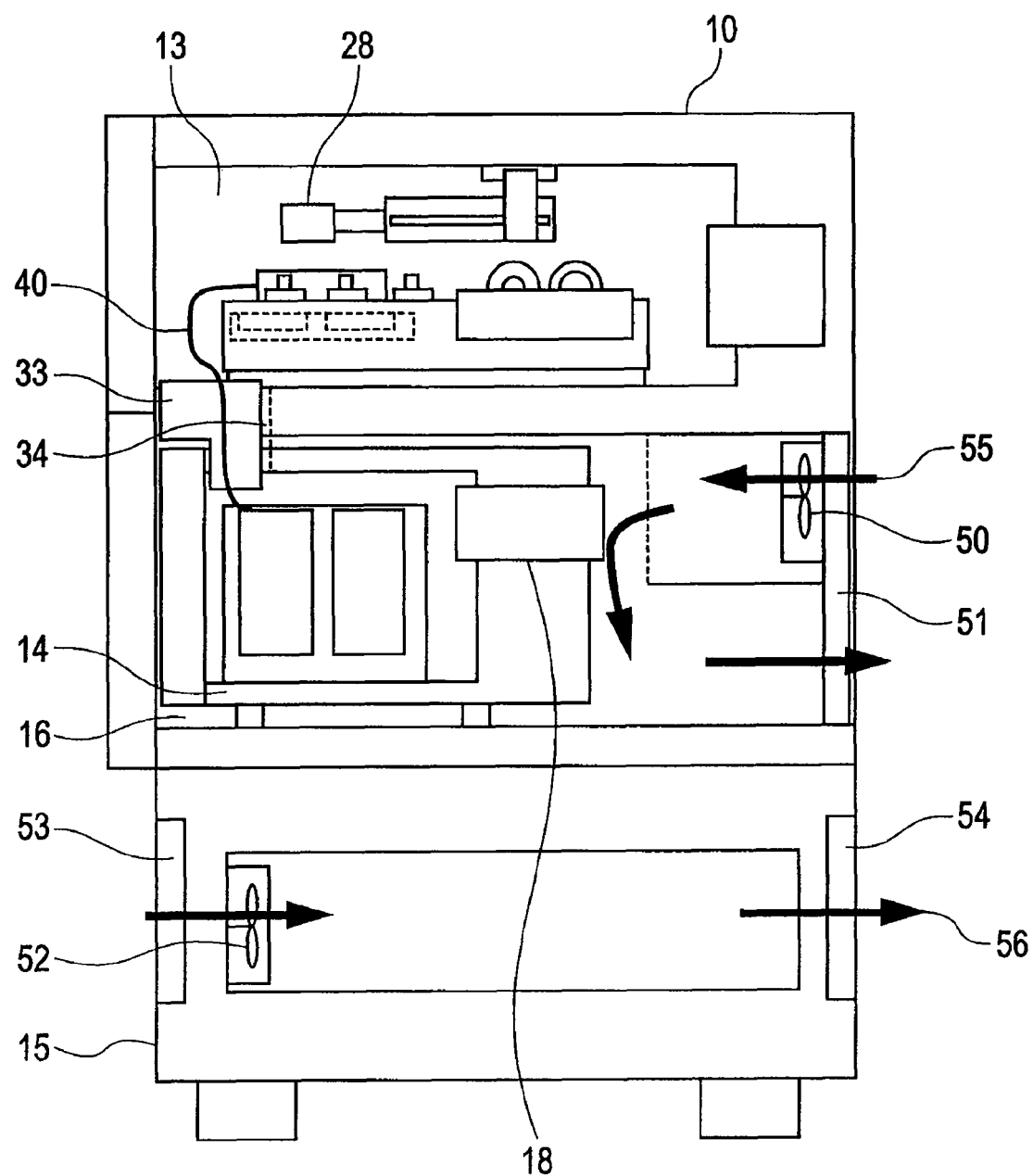
FIG. 3 is a side view showing the inside of the automatic culture apparatus in accordance with the first embodiment.
Figure 4A:
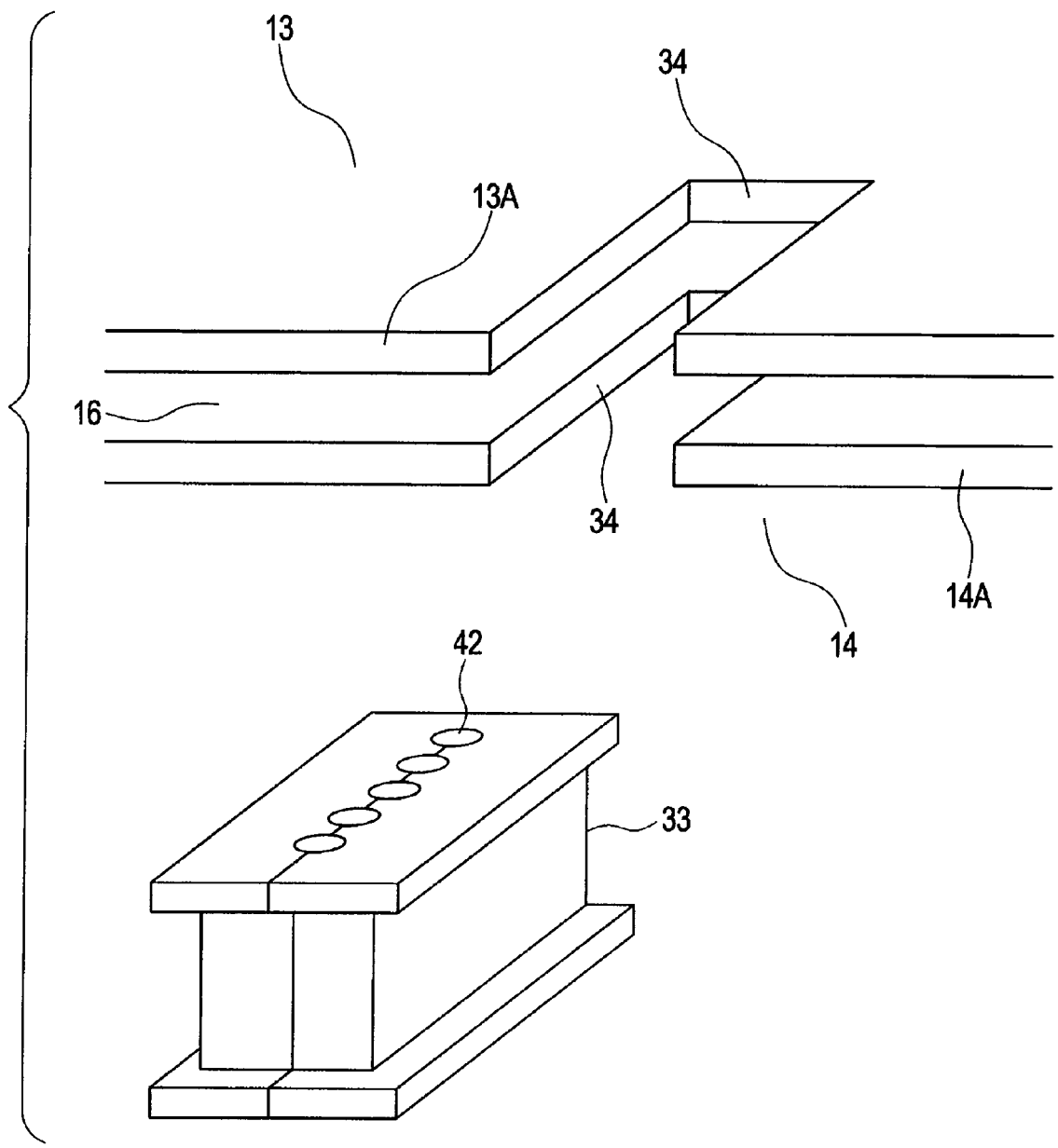
FIG. 4A is a block diagram showing a state before a seal mechanism is connected to a hook in accordance with the first embodiment.
Figure 4B:
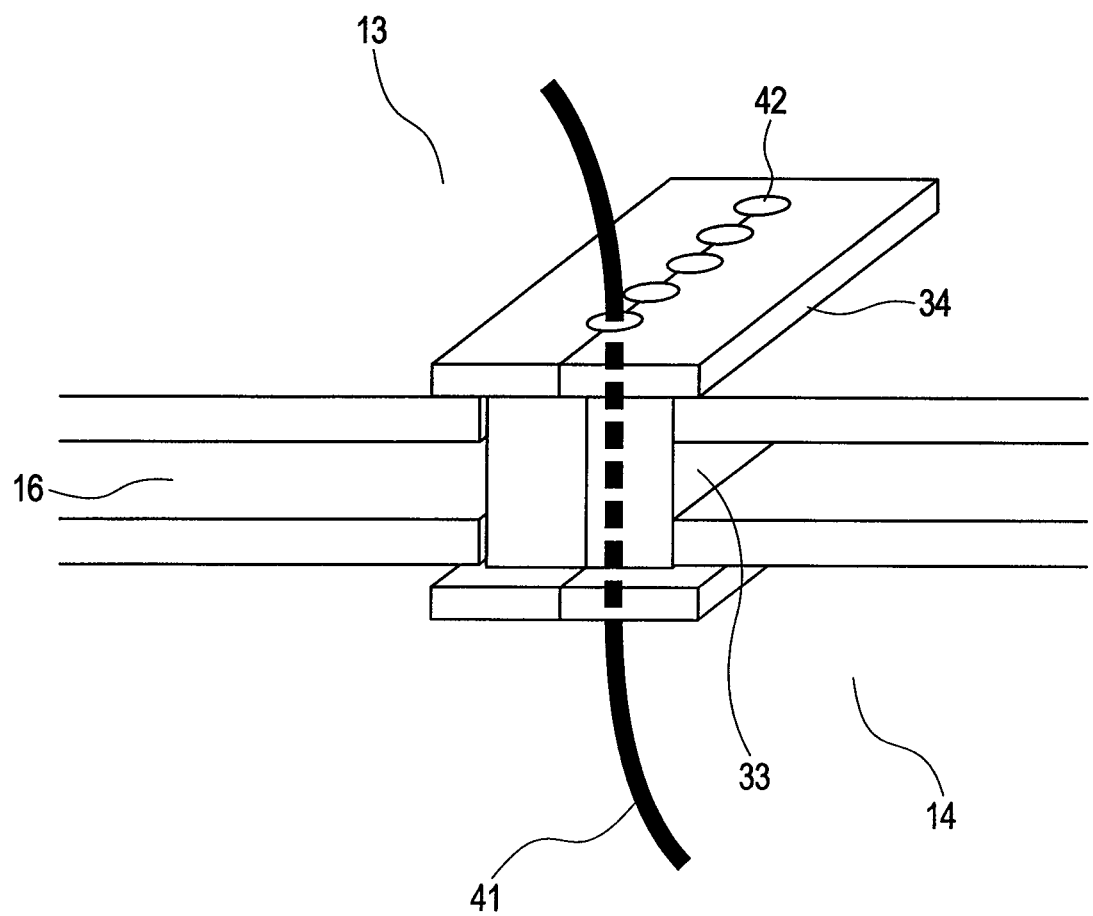
FIG. 4B is a block diagram showing a state after the seal mechanism is connected to the hook in accordance with the first embodiment.
Figure 5:
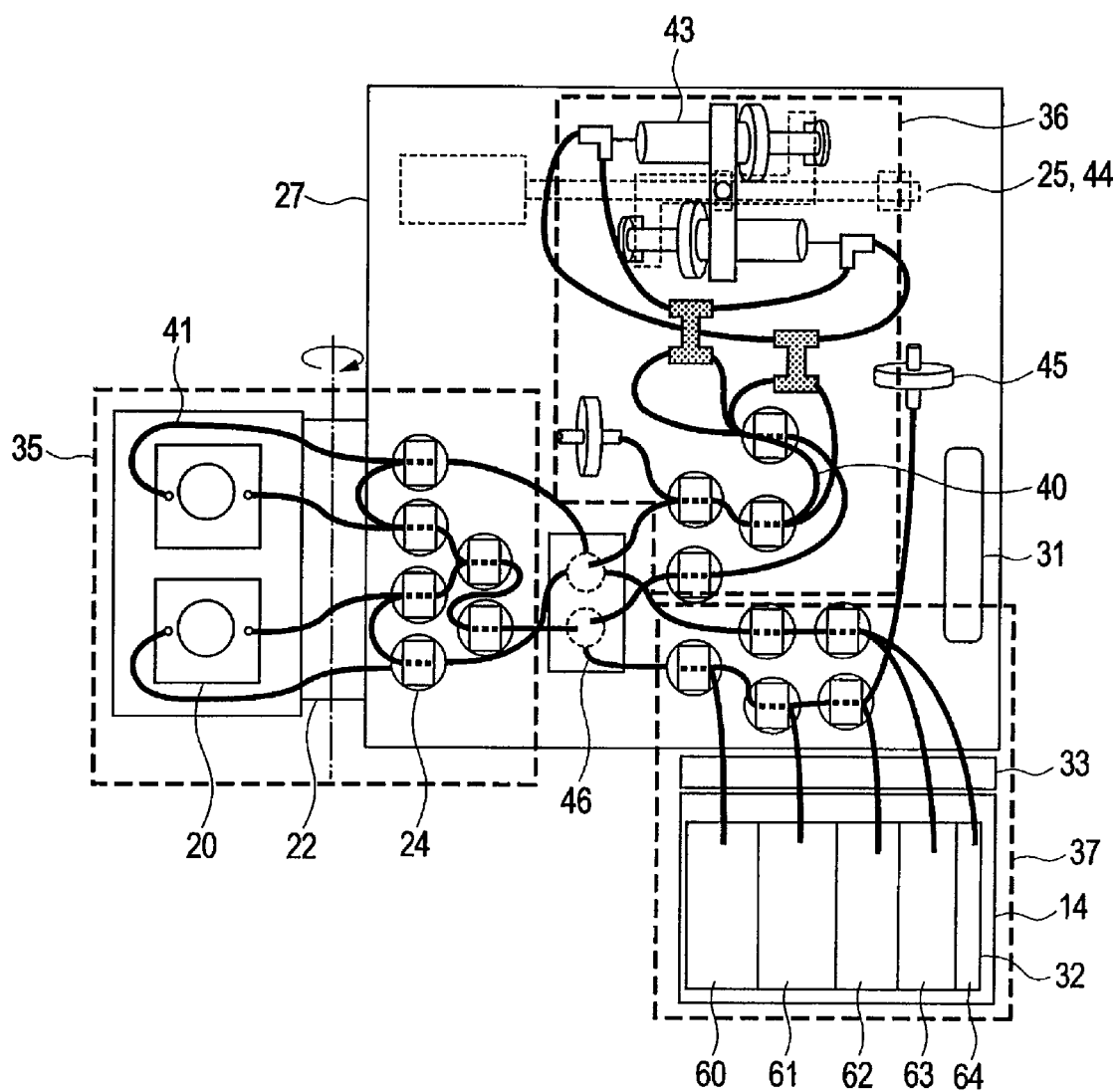
FIG. 5 is a top block diagram showing a state in which a flow channel is installed in a drive bade in accordance with the first embodiment.
Figure 6:
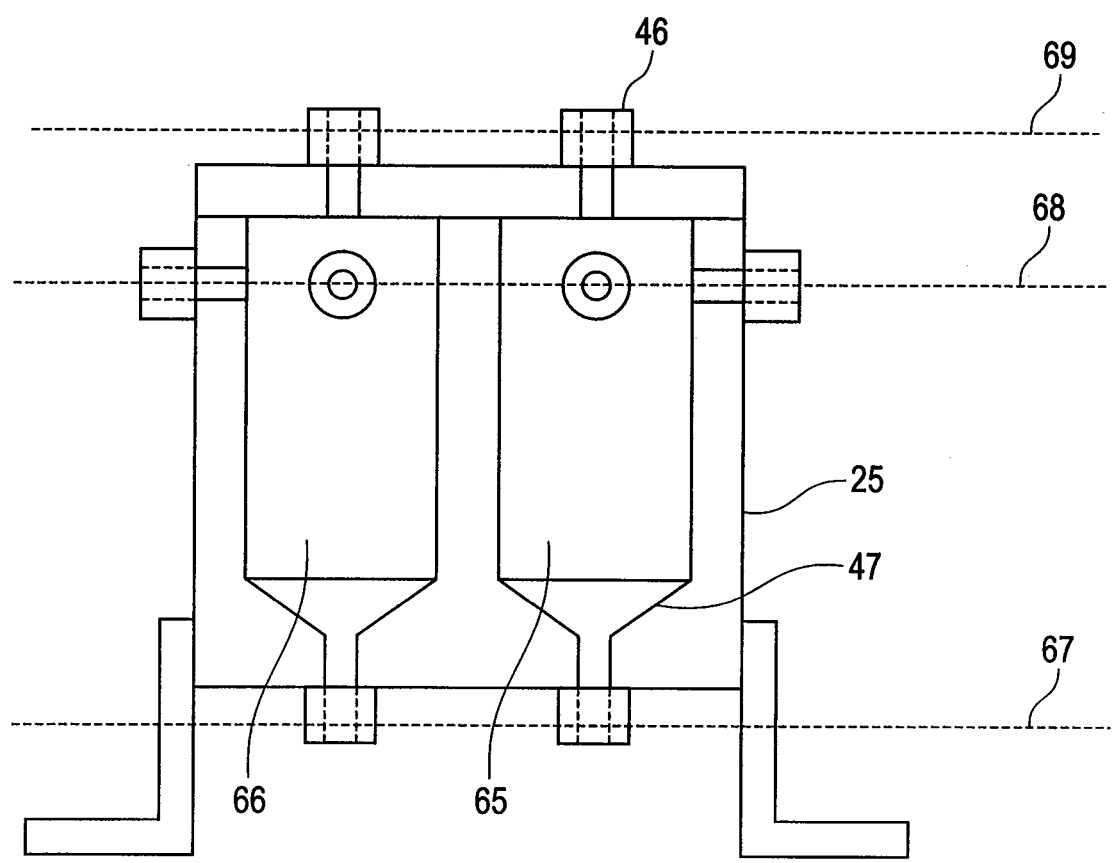
FIG. 6 is a side view showing the structure of a tank in accordance with the first embodiment.
Figure 8A:
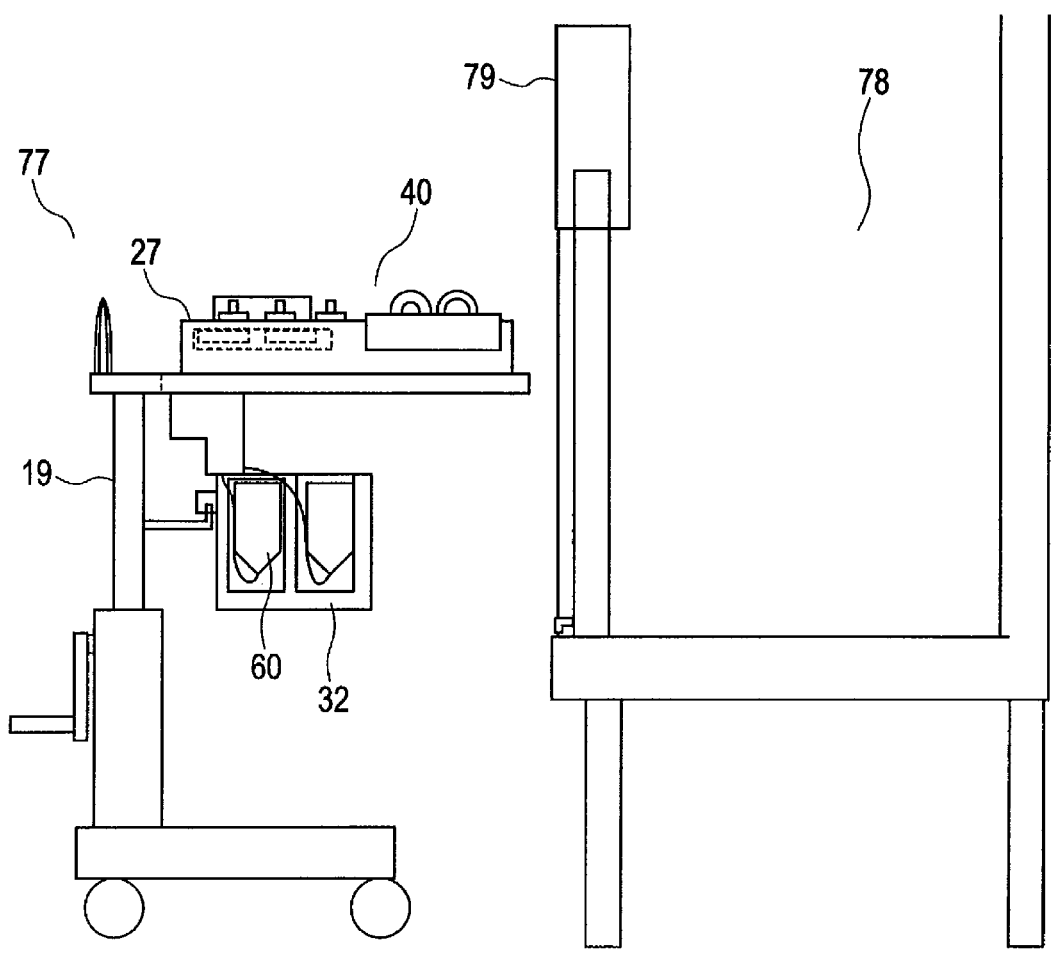
FIG. 8A is a side block diagram showing a state in which a cell suspension is not injected into a cell bag on a carrier in accordance with the first embodiment.
Figure 8B:
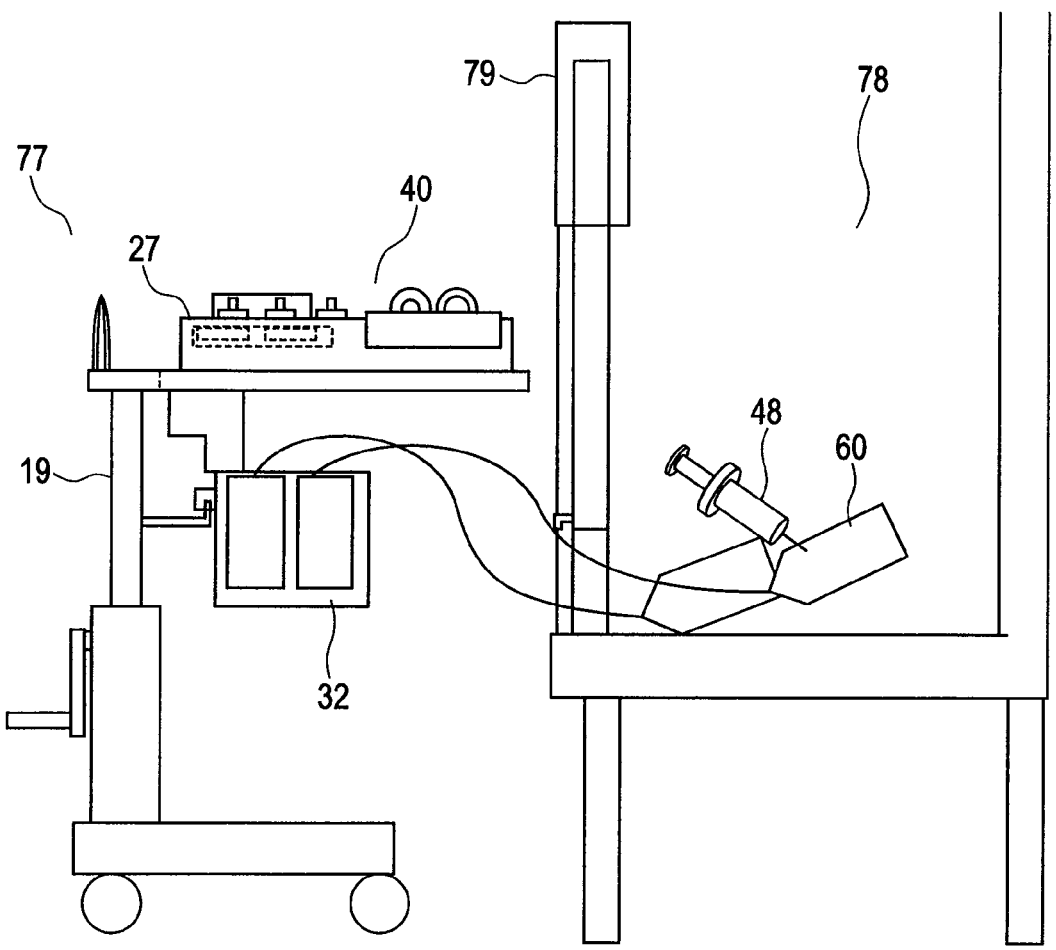
FIG. 8B is side block diagram showing a state in which the cell suspension is being injected into the cell bag on the carrier in accordance with the first embodiment.
Figure 9:
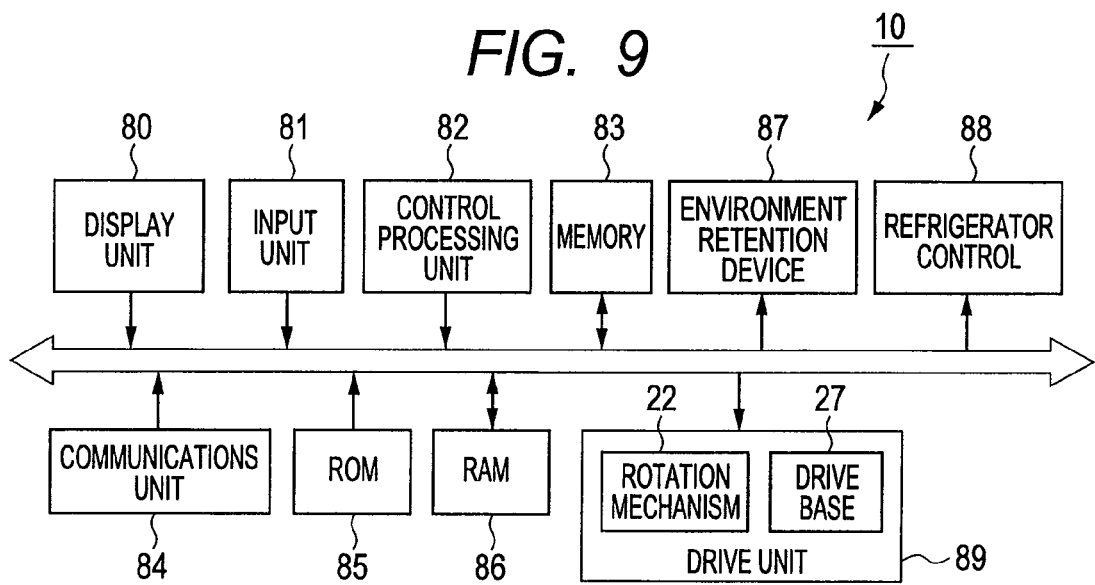
FIG. 9 is a block diagram showing the configuration of the control of the entire automatic culture apparatus in accordance with the first embodiment.

FIG. 1 is an overall schematic diagram of an automatic culture apparatus 10 in accordance with the first embodiment. FIG. 2 is a front view of the automatic culture apparatus 10. FIG. 3 is a side view of the automatic culture apparatus 10. FIGS. 4A and 4B are schematic diagrams showing a seal 33 between a cell culture chamber 13 and a refrigerator 14. FIG. 5 is a schematic diagram showing the configuration of a flow channel 40. FIG. 6 is a schematic diagram showing a tank 25 as one component of the flow channel 40. FIGS. 7A, 7B, 7C, 7D, and 7E are schematic diagrams showing a pump 23 as one component of the flow channel 40. FIGS. 8A and 8B are schematic diagrams showing aseptic delivery of a cell fluid and a culture medium to the flow channel 40. FIG. 9 is a block diagram showing a circuit for operating the automatic culture apparatus 10.

<Configuration of Automatic Culture Apparatus>

Using FIG. 1, FIG. 2, FIG. 3, and FIGS. 4A and 4B, the overall configuration of the automatic culture apparatus 10 will be described. The automatic culture apparatus 10 includes, as fundamental components, the cell culture chamber 13, the refrigerator 14, a control unit 15, and an intermediate chamber 16. Hereinafter, the fundamental structure of each component will be described.

As shown in FIG. 1, the entire automatic culture apparatus 10 includes four sections, namely, the cell culture chamber 13, the refrigerator 14 constituting the refrigerating unit, the control unit 15, and the intermediate chamber 16. Opening a cell culture chamber door 11, a refrigerator door 12, and an intermediate chamber door 17 gives access to the inside of the automatic culture apparatus 10. The cell culture chamber 13 includes a culture vessel base 21 as a holding member for holding and installing a culture vessel 20 and a rotation mechanism 22 which is connected thereto to rotate, a microscope 28 for photographing a cell image within the culture vessel 20 and its stage 29, and a drive base 27 which has drive mechanisms such as a pump 23 and a valve 24 to be connected to the flow channel 40 having a closed structure including a tank 26. It also includes a connector board 30 which is connected to all the drive mechanisms in it and is wired to the control unit 15. Wiring between the control unit 15 and the connector board 30 is not shown. During cell culturing, the inside of the cell culture chamber 13 is maintained at an environment close to a temperature of 37° C., a humidity of 100%, and a carbon dioxide of 5%. However, a structure in which only a surrounding area including the culture vessel 20 maintains the aforesaid environment may be allowed as needed. The refrigerator 14 can accommodate a culture medium base 32. The temperatures within the cell culture chamber 13 and the refrigerator 14 are maintained to allow the prevention of water condensation by a seal 33 which passes only a tube 41 of the flow channel 40, with the three sections i.e., the cell culture chamber 13, the refrigerator 14, and the intermediate chamber 16 isolated from each other. The intermediate chamber 16 is equipped with a fan 50 having a filter 51. The filter 51 is installed in a vent. Movement of air flow is caused by the fan 50 to prevent an increase in humidity. In an entrance of the intermediate chamber 16, which will be described later in detail, a seal mechanism is used for shutting down the inside of the cell culture chamber 13 and the inside of the refrigerator 14 to allow only the culture fluid to flow.

The control unit 15 is independent of the other sections and is installed below the cell culture chamber 13 and the intermediate chamber 16, thereby shutting down the temperature, humidity, and carbon dioxide within the cell culture chamber 13 to protect internal electric instruments. The control unit 15 includes a fan 52 allowing internal heat to escape to the outside aseptically by an intake filter 53 and an exhaust filter 54. The fan 52 and the filters 53, 54 constitute a cooling unit of the control unit 15. The reference numeral 57 for is a control panel of the control unit 15 and is provided with various buttons and a display unit in the same manner as normal control panels for use in the control of the control unit 15. The control unit 15 includes, needless to say, a central processing unit (CPU) and a memory as a storage unit for storing control programs and data, which are not shown.

FIG. 2 shows the arrangement of components of the automatic culture apparatus 10 with the refrigerator door 12 open when viewed from the front. With the drive base 27 within the cell culture chamber 13 as the center, a rotatable culture vessel 20 is arranged in the horizontal direction and the refrigerator 14 in which the culture medium base 32 containing the cell fluid and culture medium is installed is arranged in the vertical direction. As is clear from the drawing and FIG. 1, in the automatic culture apparatus 10 of the present embodiment, when the space (the first space) in which the drive base 27 is installed is set to be the first quadrant, the intermediate chamber 16 separating the first space and the refrigerator 14 as a refrigerating unit is positioned in the fourth quadrant, and a culture vessel base 21 as a holding member by which the culture vessel 20 is held and mounted is positioned in the second quadrant or the third quadrant by rotation. The arrangement configuration of the present embodiment is space-saving and provides a short distance between the instruments, thereby allowing the culture medium stored at around 4° C. in the refrigerator 14 positioned in the fourth quadrant to be warmed up by the tank 25 on the drive base 27 positioned in the first quadrant and to be quickly delivered to a culture space positioned in the second quadrant, thereby minimizing damage to the cells caused by movement.

As shown in FIG. 2, the microscope 28 for photographing the cells is arranged in the vertical direction from the culture vessel 20 positioned in the second quadrant when viewed from the front. The microscope 28 is fixed to the stage 29 for movement and focusing. For these arrangements, all-horizontal arrangements or all-vertical arrangements with the drive base 27 positioned in the first quadrant may be allowed, and optimum arrangement may be selected in accordance with cells to be cultured. The refrigerator 14 is within the intermediate chamber 16 positioned in the fourth quadrant. Since the sections are separated by a seal 33, the cell culture apparatus 13 and space are separated from each other except for the inside of the flow channel 40. This configuration shown in detail in FIG. 3 will be described later.

On the drive base 27, there are arranged the drive mechanisms including the pump 23 for delivering the fluid within the flow channels 40, the valve 24 for switching the fluid delivery circuit, and the tank 25 for storing the culture medium and others and performing warming up and fluid flow switching, which will be described in detail later. In order to operate the drive mechanisms, the connector board 30 is provided on the back of the drive base 27, which can be connected to a connector 31 of the drive base 27. The connector board 30 can be wired to the control unit 15. The connector board 30 connects the wiring of the connector 31 to the external control unit 15, while maintaining the environment within the cell culture chamber 13, thereby providing an adiabatic and waterproof structure. Although the control unit 15 is described in the vertical direction of the cell culture chamber 13 in the drawing, it may be installed in the horizontal direction when it is used on the desk or in a surplus space.

FIG. 3 shows the arrangements of the element devices when viewed from the side. The intermediate chamber 16 and the seal 33 are installed in order to arrange the cell culture chamber 13 and the refrigerator 14, which have utterly different environments in temperature and humidity, in the same apparatus and connect the flow channel 40 between them. Since the cell culture chamber 13 generally has 37° C. and a humidity of 100%, and the inside of the refrigerator 14 is generally maintained at 4 to 5° C., installation of the latter close to the cell culture apparatus 13 causes water condensation and temperature variations within the cell culture apparatus 13. General incubators (cell culture chambers) and refrigerators are designed on the basis of use at room temperature and room humidity. By providing the intermediate chamber 16 for maintaining a room environment in between the refrigerator 14 and the cell culture chamber 13, the occurrence of water condensation caused by a rapid temperature change is prevented. However, the culture medium, the cooling fluid, and the cell suspension within the refrigerator 14 are preferably delivered to the cell culture apparatus 13 through the tube 41 constituting the flow channel 40.

To this end, the tube 41 is passed through a channel 42 of the seal 33 and is fit into a hook 34 shown in FIGS. 4A and 4B, thereby separating the spaces of the refrigerator 14, the intermediate chamber 16, and the space of the cell culture chamber 13 from each other and allowing the culture medium, the cooling fluid, and the cell suspension to be delivered from the refrigerator 14 to the cell culture apparatus 13. The hook 34 is provided in a wall 13A separating the cell culture apparatus 13 and the intermediate chamber 16 and a wall 14A separating the refrigerator 14 and the intermediate chamber 16, respectively.

In FIG. 3, the refrigerator 14 includes a cooler 18 for cooling the inside thereof. It emits cooled heat to the outside of the refrigerator 14. In order to prevent the temperature inside the intermediate chamber 16 from rising, air passed through the filter 51 is sucked from the outside of the automatic culture apparatus 10 by the fan 50, is allowed to hit the cooler 18, and is emitted to the outside of the automatic culture apparatus 10 through the filter 51. In other words, the cooling unit of the intermediate chamber is constructed by the cooler 18, the fan 50, and the filter 51.

An air flow is indicated by an arrow 55 in FIG. 3. This allows the temperature and humidity within the intermediate chamber 16 to be maintained at the same conditions as the outside of the automatic culture apparatus 10. Many heat-producing components such as a computer and a power supply exist within the control unit 15, and heat in them has to be emitted. In order to prevent dust entering the control unit 15, air outside the control unit 15 is introduced by a fan 52 through the intake filter 53, and is then returned to the outside of the control unit 15 through the exhaust filter 54. An air flow 56 is indicated by an arrow in FIG. 3. This prevents dust from scattering in e.g. a clean space of a clean room, maintaining cleanliness.

<Configuration of Flow Channel and Drive Base>

Figure 7A:
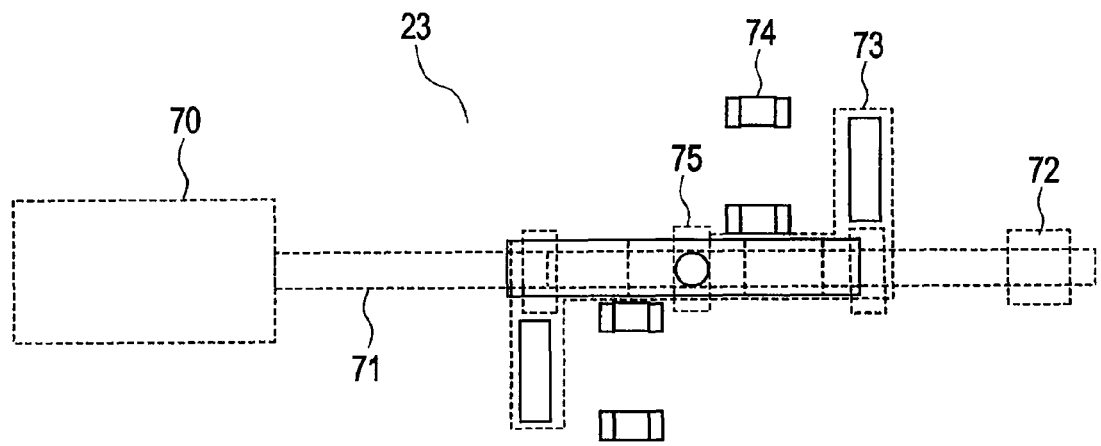
FIG. 7A is a top view showing a state before a pump is connected to a syringe in accordance with the first embodiment.
Figure 7B:
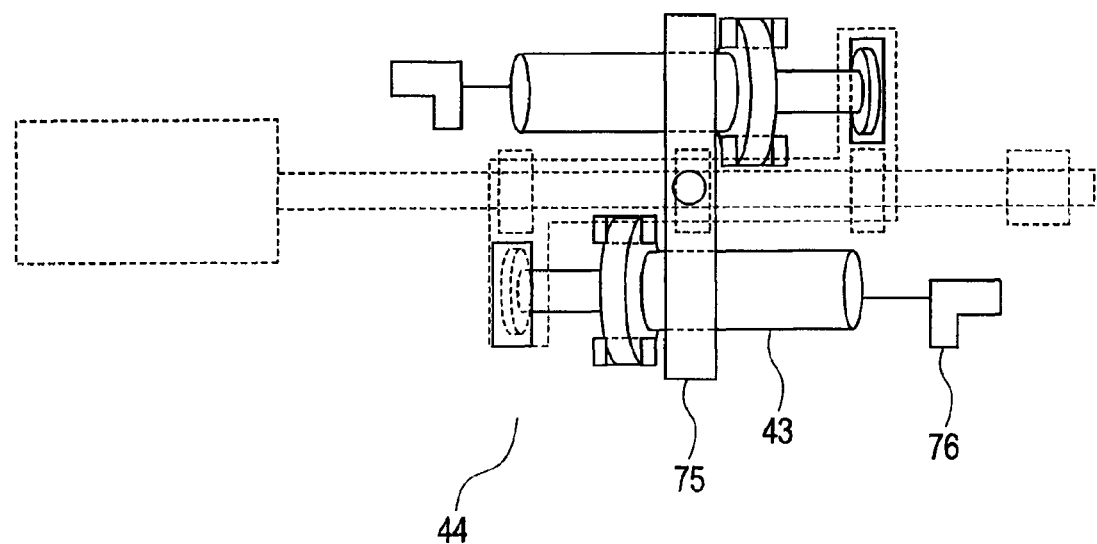
FIG. 7B is a top view showing a state after the pump is connected to the syringe in accordance with the first embodiment.
Figure 7C:
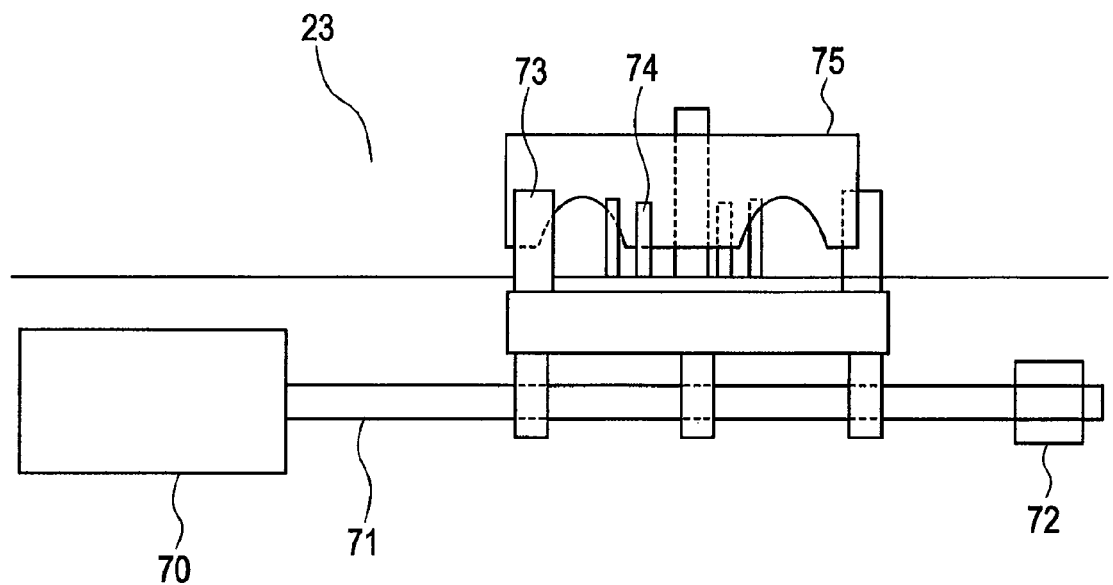
FIG. 7C is a side view showing a state before the pump is connected to the syringe in accordance with the first embodiment.
Figure 7D:
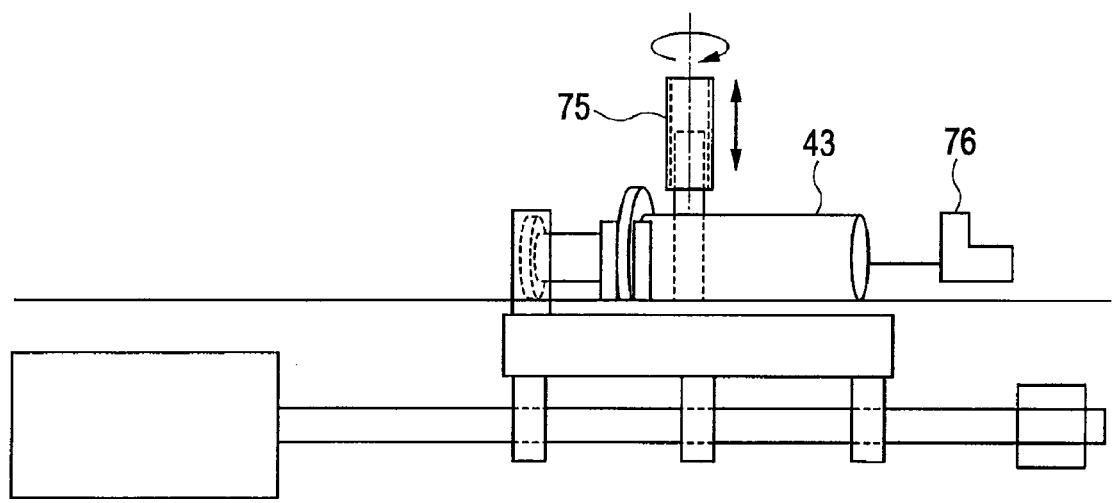
FIG. 7D is a side view showing a state in which the pump is connected to the syringe in accordance with the first embodiment.
Figure 7E:
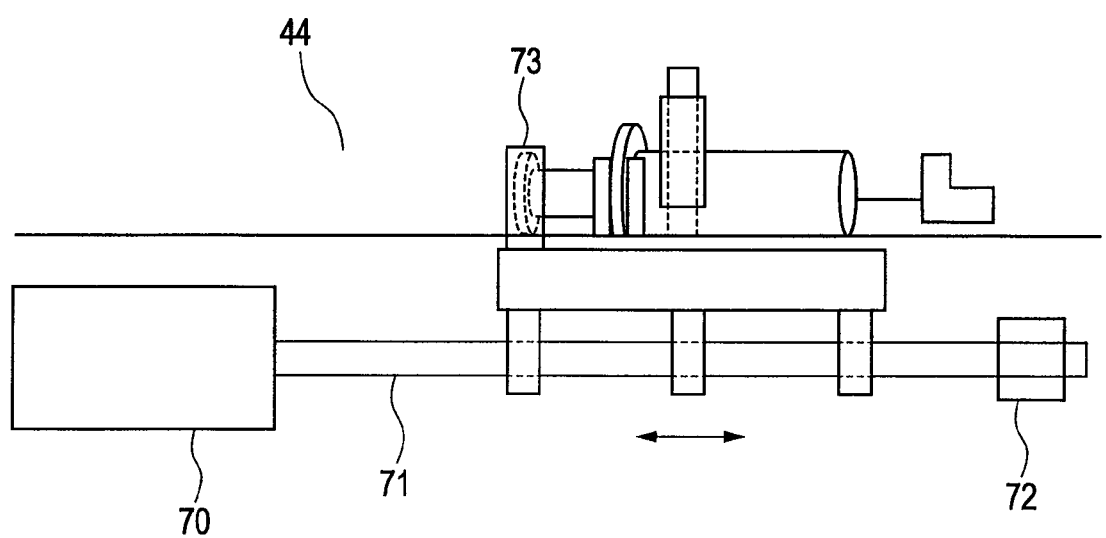
FIG. 7E is a side view showing a state after the pump is connected to the syringe in accordance with the first embodiment.

With reference to FIGS. 5, 6, and 7A to 7E, the configuration of the flow channel 40 and its drive method will be described. FIG. 5 is a schematic view showing the overall configuration of the flow channel 40 and the drive base 27. FIG. 6 is a side view showing the configuration of the tank 25. FIG. 7A shows a top view of a state in which a syringe 43 and the pump 23 are separated from each other. FIG. 7B shows a top view of a state in which the syringe 43 and the pump 23 are integral with each other. FIG. 7C shows a side view of a state in which the syringe 43 and the pump 23 are separated from each other. FIG. 7D shows a side view of a state in which the syringe 43 is set in the pump 23. FIG. 7E shows a side view of state in which the syringe 43 and the pump 23 are integral with each other to form a syringe pump 44. The syringe 43 is allowed to perform translational motion along the same axis.

First, the configuration of the flow channel 40 having a closed structure will be described with reference to FIG. 5. The flow channel 40 includes the tube 41, the culture vessel 20, the syringe 43, a filter 45, a fitting 46, the tank 25, a cell bag 60, a culture medium bag 61, a cleaning fluid bag 62, a waste fluid bag 63, and a collection bag 64, which are replaceable. The flow channel 40 is connected to the valve 24 as a drive mechanism for changing a flow direction, the pump 23 for fluid delivery, and the rotation mechanism 22 which rotates from the horizontal direction in the second quadrant to the vertical direction in the third quadrant to exclude air bubbles within the culture vessel 20, thereby allowing cell seeding and culture medium exchange through the delivery of a cell fluid and a culture medium to the culture vessel 20 and flow channel cleaning with the cleaning fluid. The rotation of the culture vessel base 21 in which the culture vessel 20 is installed from the second quadrant to the third quadrant is achieved by rotating the culture vessel base 21 from the horizontal position shown in FIG. 2 counterclockwise and downwardly by the rotation mechanism 22.

The drive mechanism is arranged in the drive base 27. Wiring and mechanisms which cannot be exposed to humidity are all accommodated in the drive base 27 to be installed in a highly humid environment. In order to be connected to the control unit 15, the drive bade 27 is provided with the connector 31, which is waterproof, and when the drive base 27 is connected to the automatic culture apparatus 10, it is connected to the connector 31, thereby operating the drive mechanism. For the arrangement of the flow channel 40, there are three independent modules with tank 25 as the center, namely, a culture vessel module 35 for performing fluid delivery to the culture vessel 20, a culture medium module 36 for delivering a culture medium within the refrigerator 14 to the tank 25, and a pump module 37 for controlling the flow (direction and flow rate) of gas in order to performing fluid delivery within the flow channel 40. This modularization can achieve optimum installation of the drive mechanism and improve the installability of the flow channel.

Referring to FIG. 6, the structure of the tank 25 as the center of the module will be described. The tank 25 includes an injection tank 65 and a waste fluid tank 66 for the culture vessel 20 and also includes a fitting 46 having different roles in accordance with height, which is divided into a first fitting 67, a second fitting 68, and a third fitting 69 in this order from below. The first fitting 67 provides fluid delivery to the culture vessel 20 on the injection tank 65 side and acts as a fluid delivery port to the waste fluid bag 63 and the collection bag 64 on the waste fluid tank 66 side. The second fitting 68 acts as an injection port for the cell suspension, the culture medium, and the cleaning fluid delivered from the culture medium module 36 to the injection tank 65 on the injection tank 65 side and acts as an injection port for the waste fluid from the culture vessel 20 to the waste fluid tank 66 on the waste fluid tank 66 side. All fluid which can be contained in the tank 25 is supposed to have an amount which does not reach the second fitting 68. The third fitting 69 is connected to the pump module 37 to be used for air flow control for fluid delivery within the flow channel 40. The tank 25 is provided with a taper 47 for preventing cells within the cell suspension from being left within the tank 25 during fluid delivery. When a fluid is delivered to the culture vessel 20 for cell seeding and culture medium exchange, it may be once warmed up within the tank 25 up to ambient temperature. A heater may be installed in the injection tank 65.

Referring to FIG. 7, the structure of the syringe pump 44 will be described. The pump 23 includes a motor 70, a ball screw 71, an encoder 72, a drive stand 73, a syringe stopper 74, and a clamp 75 in such a manner as shown in FIGS. 7A and 7C. Two facing syringes 43, to which a valve 76 for making the air flow within the syringe 43 unidirectional is connected, are installed in the syringe stopper 74 and the drive stand 73. The clamp 75 is raised and is rotated as shown in FIG. 7D to fix the syringes 43 as shown in FIGS. 7B and 7E. By the rotation of the motor 70, the drive stand 73 moves laterally through the ball screw 71 to provide repetition of suction on one side and discharge on the other side, thereby allowing continuous fluid delivery with a condition close to laminar flow. The way of arrangement of a valve 24 of the pump module 37 can exchange between discharge and suction. With the closed-system state maintained, the syringe pump 44 can be driven. Owing to precise control by the encoder 72, a necessary amount of fluid can be delivered accurately.

<Series of Operations Concerning Injection of Cell Suspension or Culture Medium into Culture Vessel>

On the basis of the structure of each part, one example of a series of cell culture operations by the automatic culture apparatus will be described. The cell suspension or culture medium is delivered to the injection tank 65 of the tank 25 by the syringe pump 44. When a predetermined amount of it is collected, gas is passed through from the filter 45 to exclude the fluid within the tube 41, and the fluid is returned to an origin position by reverse delivery, thereby allowing accurate fluid delivery next time. The cell suspension or culture medium is warmed up in the injection tank 65. The fluid is delivered to the culture vessel 20 by the syringe pump 44 through the valve 24. At that time gas and waste fluid within the culture vessel 20 are delivered to the waste fluid tank 66 side of the tank 25. The valve 24 of the pump module 37 is switched to deliver the waste fluid to the waste fluid bag 63 or the collection bag 64. The valve 24 of the pump module 37 is switched to deliver the cleaning fluid within the cleaning bag 62 to the injection tank 65 side of the tank 25. When a predetermined amount of it is collected, gas is passed through from the filter 45 to exclude the fluid within the tube 41, and the fluid is returned to the origin position by reverse delivery, thereby allowing accurate fluid delivery next time. The cleaning fluid is delivered to the waste fluid tank 66 of the tank 25 through the valve 24 so that it is not delivered to the culture vessel 20. The valve 24 of the pump module 37 is switched to deliver the waste fluid to the waste fluid bag 66. The foregoing operations are repeated a predetermined number of times during a culture period. The fluid flows unidirectionally within the flow channel 40, especially through the culture vessel module 35. This prevents the waste fluid from returning to the culture space within the culture vessel 20 and the circuit of the culture medium bag 61, thereby providing the cells with a clean, fresh culture medium all the time to maintain a clean environment free from bacteria or the like.

<Fluid Injection into Inside of Closed Flow Channel>

Referring to FIGS. 8A and 8B, an aseptic injection method for the cell suspension 48 into the flow channel 40 having a closed-system structure will be described. FIG. 8A shows a state of the drive base 27 and the culture medium base 32 without the cell suspension 48 injected into the flow channel 40, while FIG. 8B shows a state in which the cell suspension 48 is being injected into the cell bag 60 of the flow channel 40. First, the configuration of components will be described with reference to FIG. 8A. The drive base 27 and the culture medium base 32 in which the flow channel 40 is installed are installed in a carrier 19 before being installed in the automatic culture apparatus 10. The carrier 19 can install and take the drive base 27 and others in and out of the automatic culture apparatus 10, and after installation, only the carrier 19 can be taken out. An empty cell bag 60 is contained within the culture medium base 32. For example, within a Cell Processing Center (CPC) the carrier 19 can be placed in a Class 10,000 space 77. In the GMP, a cell direct processing area is only a Class 100 space within a safety cabinet 79 (including a clean bench). Hence, only a cell bag 60 carefully sterilized with ethanol or the like is put into the safety cabinet 79.

As shown in FIG. 8B, the cell suspension 48 processed within the safety cabinet 79 is injected into the cell bag 60 with a syringe or the like. After injection, the injection port is sealed to maintain the closed system of the flow channel 40. The cell bag 60 containing the cell suspension 48 is taken out of the Class 100 space 78 and is then put into the culture medium base 32. Since the flow channel 40 maintains the Class 100 space 78 through sterilization in advance, the inside of the flow channel 40 maintains the Class 100 space 78, even though the flow channel 40 is present in the Class 10,000 space 77. Even after it is installed in the automatic culture apparatus 10, since the drive mechanism is not connected to the inside of the flow channel 40, the inside of the closed flow channel 40 can maintain the Class 100 space 78 all the time regardless of space in which the automatic culture apparatus 10 is installed.

<Circuit Configuration of Automatic Culture Apparatus>

FIG. 9 shows the configuration of a control system circuit for controlling internal instruments in the automatic culture apparatus 10.

The control system circuit of the automatic culture apparatus 10 includes an input unit (a keyboard, a mouse, or the like) 81 for inputting data and instructions, a control unit 82 for controlling each operation of the automatic culture apparatus 10, a display unit 80 for presenting control conditions to a user, a ROM 85 for storing programs and parameters, a RAM 86 for temporarily storing data and processed results, a memory 83 for performing operations such as caching, a communication unit 84, an environment retention device 87 for sterilization, a heater function, a fan function, carbon dioxide supply, and water supply as well as for monitoring their conditions, a drive unit 89 provided with the rotation mechanism 22 connected to the drive base 27, and a refrigerator control 88 for controlling the environment within the refrigerator.

When a user designates a culture process to be processed from the input unit 81 and the communications unit 84, the control unit 82 sterilizes the inside of the automatic culture apparatus 10 by the sterilizing functions of the environment retention device 87 in accordance with a culture preparation program stored in the ROM 85, and after the termination of the process, carries on culture environment retention processing to make a clean environment with a temperature of 37° C., a carbon dioxide concentration of 5%, and a humidity of 100%, and at the same time performs the refrigerator control 88. The control unit 82, in accordance with an automatic culture program stored in the ROM 85, detects the setting of the drive base 27 by a position sensor. When the installation of the connector 31 is detected, cell culture processing in the culture vessel 20 is performed by the rotation mechanism 22 and the drive base 27. The processing status can be presented to the user by the display unit 80 and the communications unit 84 any time. When the cell culture processing terminates, the termination is presented to the user by the display unit 80 and the communications unit 84. When the removal or attachment of the drive base 27 is detected, the control unit 82 performs termination processing in accordance with a termination program stored in the ROM 85. As described above, a series of cell culture processing by the automatic culture apparatus 10 can be achieved.

The present invention is not limited by the above-described embodiment but includes various variations. For example, the above-described embodiment has been described in detail for good understanding of the present invention, and is not necessarily limited by one including the entire described configuration.

It is needless to say that for each structure, function, and processor of the above-described control mechanism of the automatic culture apparatus, some or all of them may be achieved by hardware through integrated circuit design and may be achieved by software through the creation of programs run by a CPU as the processor.

What is claimed is:

1. A cell culture apparatus for culturing cells using a culture medium, comprising:
    a plurality of flow channels for delivering the culture medium and the cells;
    a drive base arranged within a first space;
    a culture vessel connected to the drive base through the flow channels;
    a holding member for holding the culture vessel;
    a refrigerating unit which is formed below the drive base to form a refrigerating space, the refrigerating unit configured to store the culture medium and the cells;
    an intermediate chamber for separating the first space and the refrigerating space, wherein a temperature of the intermediate chamber is lower than a temperature of the first space, and higher than a temperature of the refrigerating space; and
    a detachable flow channel holding member that holds the flow channels connecting the refrigerating unit with the drive base, and connects the first space, the intermediate chamber, and the refrigerating space,
    wherein the detachable flow channel holding member is a seal for spatially separating the first space, the refrigerating space, and the intermediate chamber.

2. The cell culture apparatus according to claim 1, wherein the intermediate chamber is provided with a cooling unit for cooling the intermediate chamber.

3. The cell culture apparatus according to claim 1, wherein the holding member is arranged in a second quadrant with respect to the first space as a first quadrant.

4. The cell culture apparatus according to claim 1, wherein the intermediate chamber is arranged in a fourth quadrant with respect to the first space as a first quadrant.

5. The cell culture apparatus according to claim 1, further comprising a pump and a valve for delivering the culture medium and the cells within the flow channels and a control unit for controlling the pump and the valve,
    wherein the pump, the valve, and part of the flow channels are installed on the drive base.

6. The cell culture apparatus according to claim 5, wherein the pump has a syringe which can perform translational motion along the same axis.

7. A cell culture apparatus for culturing cells, comprising:
    a plurality of flow channels for delivering a culture medium and a cell fluid;
    a drive base arranged within a first space;
    a culture vessel connected to the drive base through the flow channels;
    a culture vessel base which is arranged in a second quadrant with respect to the first space as a first quadrant and in which the culture vessel is installed;
    a refrigerating unit for refrigerating the culture medium and the cell fluid;
    an intermediate chamber which is positioned below the drive base and in a fourth quadrant with respect to the first space and separates the refrigerating unit installed therein and the first space, wherein a temperature of the intermediate chamber is lower than a temperature of the first space, and higher than a temperature of the refrigerating space; and
    a detachable seal mechanism which holds the flow channels which deliver the culture medium and the cell fluid held in the refrigerating unit, and connects the first space, the intermediate chamber and the refrigerating unit,
    wherein the seal mechanism spatially separates the first space, the refrigerating space and the intermediate chamber.

8. The cell culture apparatus according to claim 7, further comprising:
    a tank and a pump connected to the flow channels and a valve for opening and closing the flow channels installed on the drive base; and
    a control unit for controlling the pump and the valve.

9. The cell culture apparatus according to claim 8, wherein the pump has a syringe which can perform translational motion along the same axis.

10. The cell culture apparatus according to claim 8, wherein the flow channels are attachable and detachable to and from the pump and the valve.

11. The cell culture apparatus according to claim 8,
    wherein the control unit is provided with a cooling unit for cooling the control unit, and
    the control unit is positioned below the cell culture chamber and the intermediate chamber.

12. The cell culture apparatus according to claim 7, wherein the intermediate chamber is provide with a cooling unit for cooling the intermediate chamber.

13. The cell culture apparatus according to claim 7, further comprising a rotation mechanism which can rotate the culture vessel base from a position in the second quadrant to a position in a third quadrant with respect to the first space.

* * * * *